United States Patent [19]
Fraser

[11] Patent Number: 5,267,944
[45] Date of Patent: Dec. 7, 1993

[54] METHOD FOR USE IN HIP SPICA CAST APPLICATION

[76] Inventor: Keith E. Fraser, 1 Claridge Dr., Verona, N.J. 07044

[21] Appl. No.: 965,210

[22] Filed: Oct. 23, 1992

[51] Int. Cl.⁵ .......................... A61F 5/00; A61G 15/00
[52] U.S. Cl. ......................................... 602/8; 128/845
[58] Field of Search ................... 602/4, 5, 6, 7, 8, 9, 602/19, 23; 128/845, 869-876; 5/120-122

[56] References Cited

U.S. PATENT DOCUMENTS

| | | | |
|---|---|---|---|
| 224,784 | 2/1880 | Johnstone | 602/8 |
| 4,117,840 | 10/1978 | Rasure | 128/874 |
| 4,375,110 | 3/1983 | Murphy | 5/122 |
| 4,672,958 | 6/1987 | Garman | 128/873 |
| 5,208,925 | 5/1993 | Edlund | 128/875 |

*Primary Examiner*—Michael A. Brown
*Attorney, Agent, or Firm*—R. Neil Sudol; Henry D. Coleman

[57] ABSTRACT

A medical technique comprises the steps of attaching a hammock to the head rail and foot rail of a crib, and placing a child in the hammock. A hip spica cast is applied around the legs and a portion of the torso of the patient, as well as a portion of the hammock. The cast is dried while maintaining the patient in the hammock. Subsequently, an end portion of the hammock is pulled through the cast to separate the hammock from the cast and the patient upon completion of the drying.

11 Claims, 3 Drawing Sheets

5,267,944

METHOD FOR USE IN HIP SPICA CAST APPLICATION

BACKGROUND OF THE INVENTION

This invention relates to a method for use applying a hip spica cast to a patient, particularly to a child or infant.

Hip spica cast immobilization is frequently indicated in the treatment of both traumatic and atraumatic conditions where the joints above and below the femur must be immobilized. The technique is used in both children and adults. However, it is most commonly performed in children because of its simplicity, effectiveness, and minimal morbidity in young patients. Because of the substantial manipulation necessary to complete the procedure, most children become over-aroused, over-stimulated, and defy optimal cooperation. For this reason, many surgeons apply hip spica casts in an operating room setting where the child's level of anesthesia and, hence, cooperation can be more entirely controlled. Commercial hip spica tables for the pediatric patient are not always readily available, and few institutions can justify the cost of purchase of such a seldom used specialty device.

During a conventional procedure utilizing a hip spica cast table, the child is placed on the table and the cast is applied about the child and a portion of the table. Subsequent to cast hardening or curing, the table is dissassembled. During the disassembly, a portion of the table is removed from the cast, thereby detaching the child from the table.

Hip spica cast application tables are not only expensive, they are uncomfortable for the child. In addition, a table has a fixed size and is accordingly limited in the range of patient sizes which can be accommodated.

OBJECTS OF THE INVENTION

An object of the present invention is to provide an alternative method for use in hip spica cast application.

Another object of the present invention is to provide such a method which is simple and safe and which requires only readily available materials.

Another, more particular, object of the present invention is to provide such a method which is well tolerated by infants.

A further particular object of the present invention is to provide such a method which requires a minimum of skilled assistance.

Yet another particular object of the present invention is to provide a hammock suspension technique for hip spica cast application.

These and other objects of the present invention will be apparent from the drawings and detailed descriptions herein.

SUMMARY OF THE INVENTION

A medical method comprises, in accordance with the present invention, the steps of (a) placing a patient in a flexible suspension member, (b) applying a hip spica cast around a portion of the torso of the patient, at least one leg of the patient, and a portion of the suspension member, (c) drying the cast while maintaining the patient in the suspension member, and (d) pulling an end portion of the suspension member through the cast to separate the suspension member from the cast and the patient upon completion of the step of drying.

Pursuant to another feature of the present invention, the method also comprises the step, performed prior to the placement of the patient on the suspension member, of attaching the suspension member to a head support and a foot support. Preferably, the suspension member is attached to the head support at two spaced points and to the foot support at essentially one point. Accordingly, the suspension member is tapered and is wider at a head end to support the shoulders and torso of the patient.

In accordance with another feature of the present invention the method includes step of adjusting the suspension member to accommodate the size of the patient. This adjustment may be accomplished by changing the distance between the spaced points at which the suspension member is attached to the head support. This adjustment widens or narrows the head strip or head portion of the suspension member and permits adaptation of the suspension member to the specific torso and shoulder dimensions of the patient.

Where the suspension member is tapered from the head support towards the foot support, a narrow end portion of the suspension member is preferably pulled through the cast upon completion of the drying process.

Preferably, the head support and the foot support have approximately the same height and advantageously take the form of a head rail and a foot rail of a crib. In that case, particularly appropriate for children, the suspension member is suspended above a mattress of the crib, providing a protective catch for the patient.

Pursuant to another feature of the present invention, the method further comprises the step of wrapping a sheet (such as a severed stockinette) about the patient and the suspension member prior to the application of the cast. Without the stockinette strip, as the sheet or suspension member is withdrawn from the cast at the end of the casting procedure, the cast padding will curl and roll underneath the cast, creating an undesirable condition for the child's skin. Accordingly, the use of a stockinette strip is recommended.

The suspension member used in a method in accordance with the present invention may be made of a sheet, towel or other sheet material and may simply take the form of a hammock or sling.

A hammock or sling suspension technique in accordance with the present invention utilizes a classic proven suspension environment to support a child during hip cast immobilization. The materials necessary for the technique are all readily available at all hospitals and facilities. The technique may be used at a crib with materials conventionally found in cribs. The technique is therefore economical.

The hammock or sling suspension technique in accordance with the present invention is exceptionally well tolerated by children. Accordingly, anesthesia or sedation is rarely required. This enables the use of the technique at the bedside and the acute care environment.

Because the suspension member, specifically a hammock, provides broad, adaptable support, the entire hip cast application procedure can be performed by a single surgeon and an unskilled assistant.

A suspension member as used in accordance with the present invention is supple and may be evenly distributed under and about a child's torso. This advantage minimizes the tactile stimulation to the child. In addition, the classic hammock rocking motion and conforming attributes of the suspension environment provide a soothing support envelope for the child, unlike cold and hard surfaces of standard commercial hip spica tables. Most children are calm or even asleep during the procedure.

Another advantage of the procedure of the instant invention is adaptability. In contrast to conventional casting tables, the system can be fashioned to an infinite number of dimensions to specifically fit an infant of any size.

DETAILED DESCRIPTION

Figure 1:
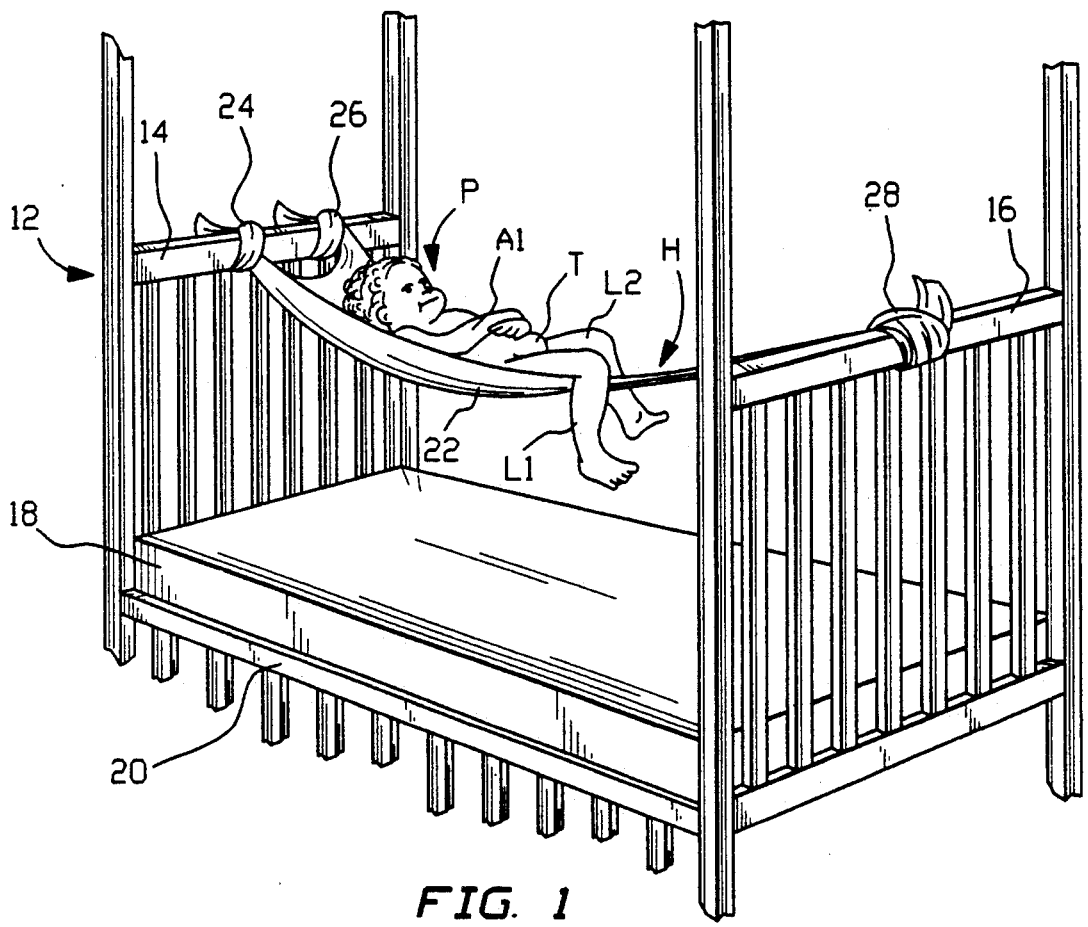
FIG. 1 is a perspective view of a child patient suspended in a hammock at the beginning of a hip spica cast application procedure in accordance with the present invention.

As illustrated in FIG. 1, a method in accordance with the present invention is suited for the bedside and can be performed within a conventional crib 12 with a head rail 14 and a foot rail 16 at approximately the same height one to two feet above the level of a mattress 18. The side rails 20 are lowered. A sheet, blanket, towel or other flexible web 22 is folded so that its length spans in excess the length of crib 12 and more particularly the distance between head rail 14 and foot rail 16. The folded sheet 22 has a width approximately 1.5 to 2 times the width of the child patient P.

Folded sheet 22 is attached at two spaced points 24 and 26 on head rail 14 or other support. The remaining two corners of sheet 22 are brought together and secured to foot rail 16 (or other, equivalent support) in a single adjustable knot 28 to create a hammock H in which child P is placed.

Figure 2:
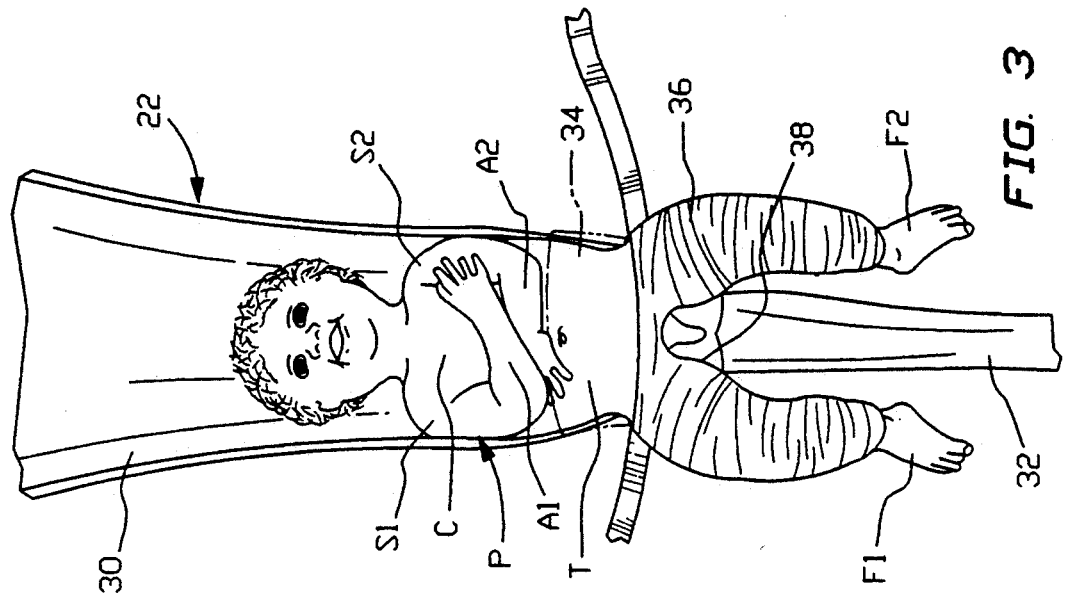
FIG. 2 is a partial top view of the child and hammock of FIG. 1, schematically showing a second step in the procedure.

Knot 28 is adjusted while tying to achieve a comfortable and appropriate tension for hammock H. Attachment points 24 and 26 on head rail 14 are moved towards or away from one another to allow the hammock to sufficiently support the shoulders S1 and S2 and torso T of child P. As illustrated in FIG. 2, hammock H tapers in a direction from head rail 14 to foot rail 16 so that under the child's shoulders S1 and S2 is a relatively broad strip 30, while under the buttocks BB of child P is a narrow strip 32 which emerges from between legs L1 and L2 of child P.

As illustrated in FIG. 1, legs L1 and L2 of the child P dangle from each side of hammock H and particularly narrow strip 32. Arms A1 and A2 of child P are folded gently over the chest C. Alternatively, an assistant (not shown) supports one or both arms A1 and A2 to keep these extremities out of the way during cast application. Supporting one or both arms A1 and A2 assists in the fine balancing of hammock H.

Upon the placement of child P in hammock H, a wide stockinette strip 34 is wrapped around torso T and buttocks BB of child P, as well as around hammock H, as illustrated in dashed lines in FIG. 2. The stockinette strip 34 is obtained by dividing or cutting a tubular stockinette. Although an intact stockinette may be applied, such a procedure would require inserting sheet 22 through the stockinette prior to fixation of hammock H to head rail 14 and foot rail 16. It is substantially simpler to divide a tubular stockinette segment into a web or sheet and to wrap that sheet around both the child P and hammock H after placement of child P into hammock H. Additional stockinettes 35a and 35b may be applied to legs L1 and L2. Without stockinette strip 34, as sheet 22 is ultimately withdrawn from the hip spica cast, the cast padding will curl and roll underneath the cast, creating an unfavorable condition for the child's skin. Accordingly, the use of stockinette strip 34 is recommended.

Generally, stockinette is applied entirely over all areas over which the cast will be applied. A cast padding layer (not shown) is applied over stockinettes 34, 35a and 35b prior to the application of a final layer consisting of cast material. Stockinettes 34, 35a, and 35b are incorporated into the cast and form a secured durable intact layer against the skin of the patient which helps to maintain the integrity and uniformity of the overlying cast padding layer, particularly during withdrawal of hammock H.

Torso stockinette 34 encircles both the patient's torso T and hammock H and is extended just proximal to the naval of the child P. Torso stockinette 34 and leg stockinettes 35a and 35b ideally overlap with one another. Whereas torso stockinette 34 is applied about both hammock H and torso T, leg stockinettes 35a and 35b are applied around legs L1 and L2 only and are independent of hammock H.

Upon application of a layer of cast padding and an initial layer of cast material, excess free margins of the stockinettes 34, 35a, 35b are folded over the exterior of the cast margins. Final layers of cast materials are then applied, securing the free margins of the stockinette into the formed cast. This procedure also has the effect of padding the abrasive free edges of the final cast.

Figure 3:
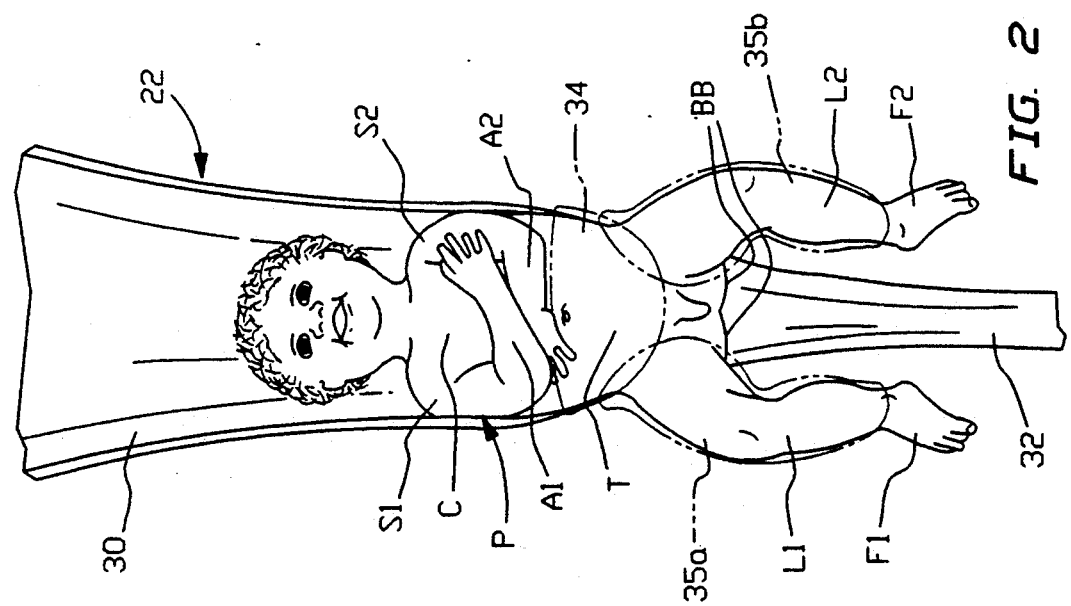
FIG. 3 is a partial top view of the child and hammock of FIGS. 1 and 2, illustrating application of a hip spica cast in a procedure in accordance with the present invention.

As depicted in FIG. 3, the remainder of the hip spica cast 36 is applied in the conventional manner. Tail or narrow strip 32 emerges from a perineal opening 38. Legs L1 and L2 are positioned within cast 36 to satisfy the existing clinical conditions.

During drying of cast 36, an assistant (not shown) may support each foot F1 and F2. Child P rests comfortably in hammock H for the duration of the drying process.

Figure 4:
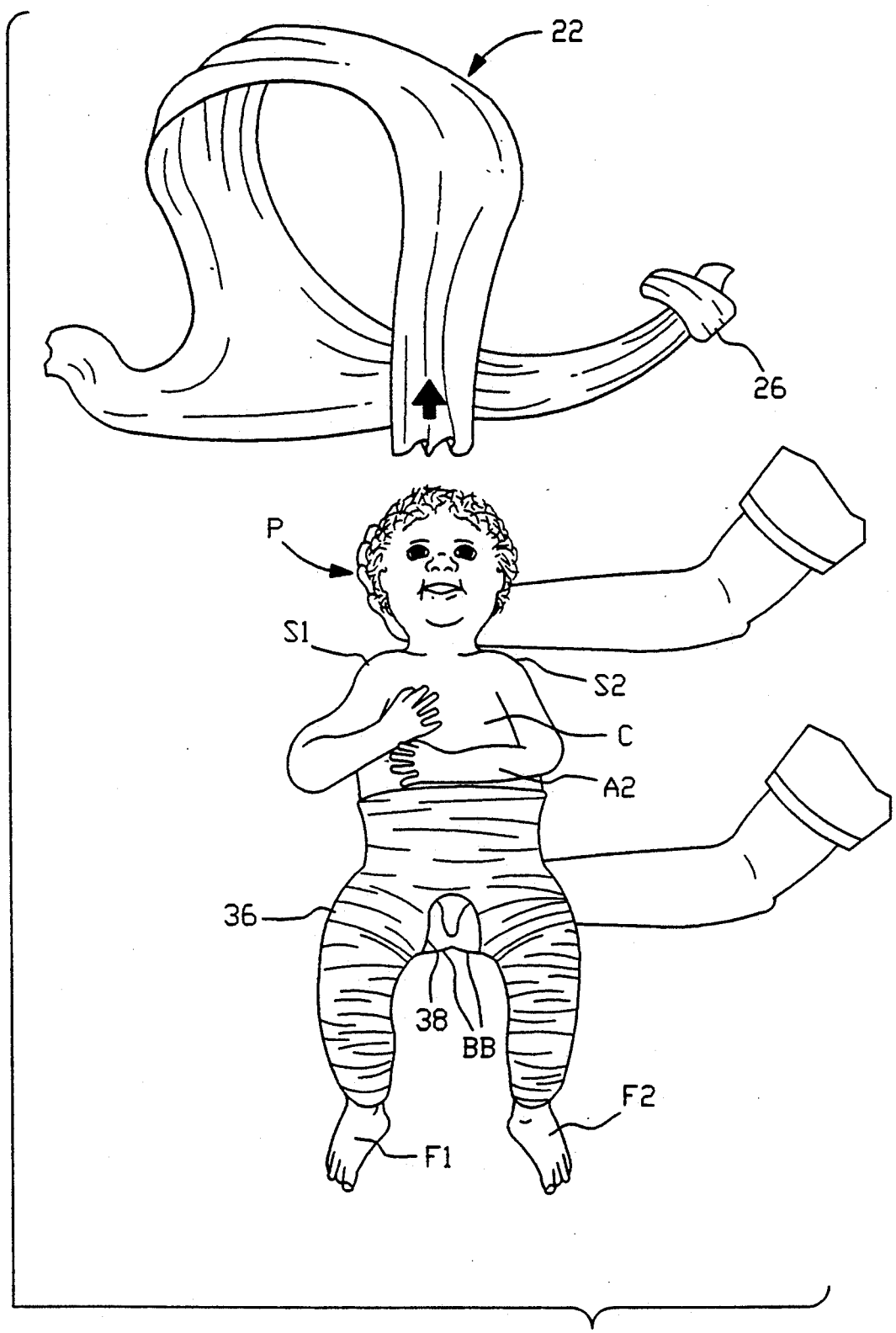
FIG. 4 is a partial top view of the child and hammock of FIGS. 1—3, illustrating a final step in a hip spica cast application procedure in accordance with the present invention.

Upon a satisfactory setting of cast 36, child P is removed from hammock H by untying knot 28 and withdrawing sheet 22 between legs L1 and L2, through perineal opening 38 and within cast 36 until the child is completely free of hammock H, as illustrated in FIG. 4.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by wa of example to facilitate comprehension of the invention and should not be construed to limit the scope thereof.

What is claimed is:
1. A medical method comprising the steps of:
placing a patient in a flexible suspension member;

applying a hip spica cast around a portion of the torso of the patient, at least one leg of the patient, and a portion of the suspension member;

drying the cast while maintaining the patient in the suspension member; and upon completion of said step of drying, pulling an end portion of the suspension member through the cast to separate the suspension member from the cast and the patient.

2. The method defined in claim 1, further comprising the step, performed prior to said step of placing, of attaching said suspension member to a head support and a foot support.

3. The method defined in claim 2 wherein said suspension member is attached to said head support at two spaced points and to said foot support at essentially on point.

4. The method defined in claim 3, further comprising the step of adjusting the suspension member to accommodate the size of the patient.

5. The method defined in claim 4 wherein said step of adjusting includes the step of changing the distance between said spaced points.

6. The method defined in claim 3 wherein said suspension member is tapered from said head support towards said foot support, a narrow end portion of said suspension member being pulled through said cast upon completion of said step of drying.

7. The method defined in claim 1 wherein said suspension member is made of sheet material.

8. The method defined in claim 1 wherein said suspension member is a hammock.

9. The method defined in claim 1 wherein said head support and said foot support have approximately the same height.

10. The method defined in claim 1 wherein said head support and said foot support are a head rail and a foot rail of a crib, said suspension member being suspended above a mattress of said crib.

11. The method defined in claim 1, further comprising the step of wrapping a sheet about the patient and said suspension member prior to said step of applying.

* * * * *